(12) United States Patent
Kunz et al.

(10) Patent No.: US 6,483,096 B1
(45) Date of Patent: Nov. 19, 2002

(54) INTEGRATED-OPTICAL CHEMICAL AND BIOCHEMICAL SENSOR

(75) Inventors: Rino E. Kunz, Steinmaur (CH); Guy Voirin, Saint-Aubin (CH); Philipp N. Zeller, Zollikerberg (CH)

(73) Assignee: Csem Centre Suisse D'Electronique et de Microtechnique SA, Neuchatel (CH)

( * ) Notice: Subject to any disclaimer, the term of this patent is extended or adjusted under 35 U.S.C. 154(b) by 11 days.

(21) Appl. No.: 09/660,978

(22) Filed: Sep. 13, 2000

(30) Foreign Application Priority Data

Sep. 15, 1999 (EP) .............................. 99118309

(51) Int. Cl.$^7$ .............................................. H01J 40/14

(52) U.S. Cl. ............................. 250/214 R; 250/561.1; 385/12

(58) Field of Search ................... 250/458.1, 459.1, 250/467.1, 214 R; 356/417, 311, 317, 318; 385/12, 10; 436/518

(56) References Cited

U.S. PATENT DOCUMENTS 5,081,012 A * 1/1992 Flanagan et al. .......... 356/73.1
6,211,954 B1 * 4/2001 Danielzik ................... 356/317
6,312,961 B1 * 11/2001 Voirin et al. ............... 356/317

OTHER PUBLICATIONS

WO 97/37211, Oct. 9, 1997, Integrated Optical Luminescence Sensor.
"Miniature integrated optical modules for chemical and biochemical sensing$^1$", R.E. Kunz, Sensors and Actuators B, vol. B38, No. 1–3, Feb. 1997, pp. 13–28, XP004083666, ISSN 0925–4005.

"Waveguides as chemical sensors", Raymond E. Dessy, Analytical Chemistry, vol. 61, No. 19, Oct. 1989, pae 1079A–1094A, XP000088109, ISSN 0003–2700.

* cited by examiner

Primary Examiner—Stephone Allen
Assistant Examiner—Bradford Hill
(74) Attorney, Agent, or Firm—Rankin, Hill, Porter & Clark LLP

(57) ABSTRACT

The integrated-optical chemical and/or biochemical sensor comprises a resonant waveguide structure (1). A chemical and/or biochemical substance (2) to be sensed can be deposited on a surface of the waveguide structure (1). Incident light (31) is coupled into the waveguide structure (1) by a grating structure (G), making use of a first set of degrees of freedom. The incoupled light (32) interacts with the substance (2), which emits fluorescent light (42). Fluorescent light (42) is coupled out by the same grating structure (G), making use of a second set of degrees of freedom which differs from the first set of degrees of freedom in at least one degree of freedom. For example, the incident light (31) is coupled in using a first diffraction order $m_{g,ex}=1$, and the emitted (42) light is coupled out using a second, different diffraction order $m_{g,em}=2$. By this measure, the emitted outcoupled light (43) is clearly separated from exciting light (33) which is reflected and/or coupled out using the first diffraction order $m_{g,ex}=1$. Such a clear separation increases the signal-to-noise ratio of the sensor signal.

13 Claims, 16 Drawing Sheets

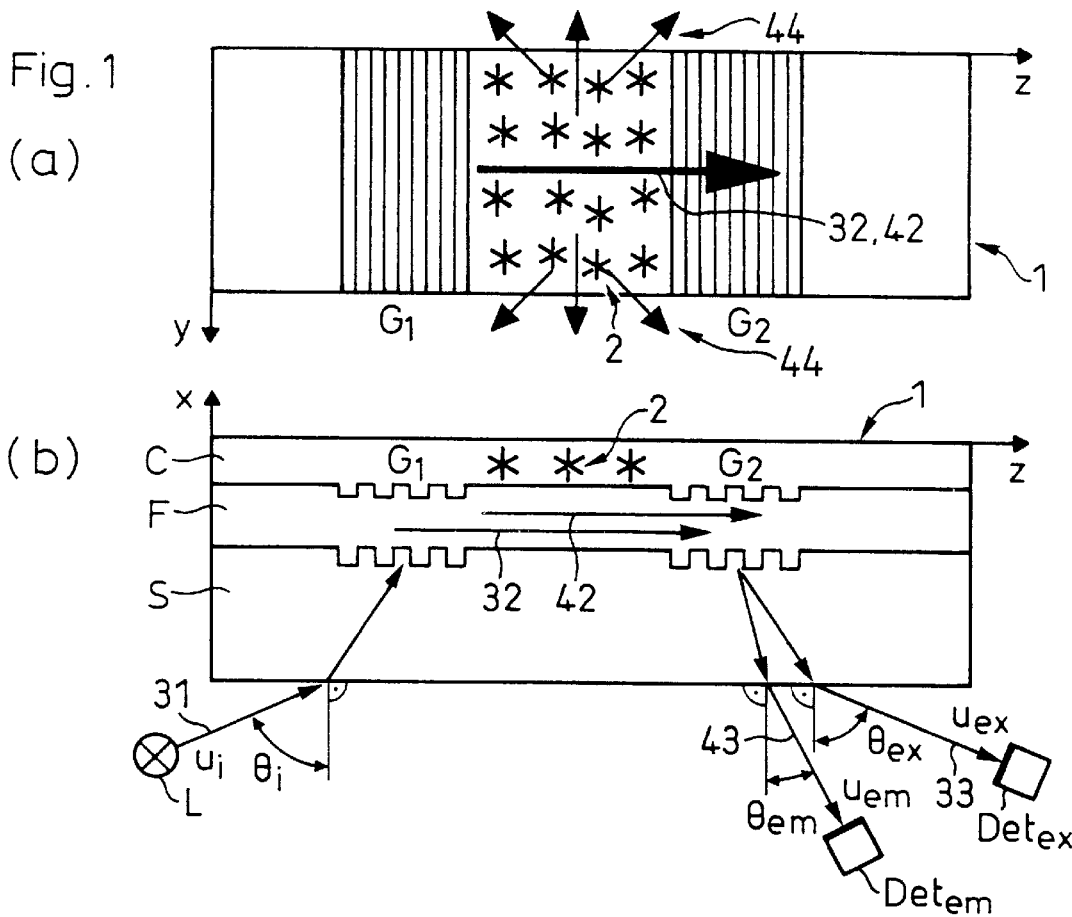
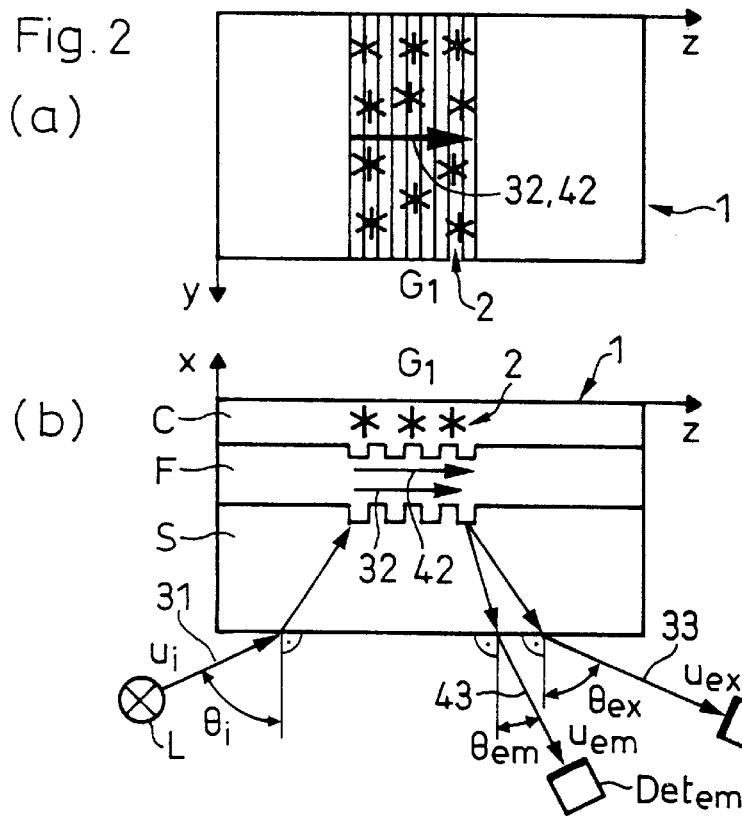

Fig. 3
(a)
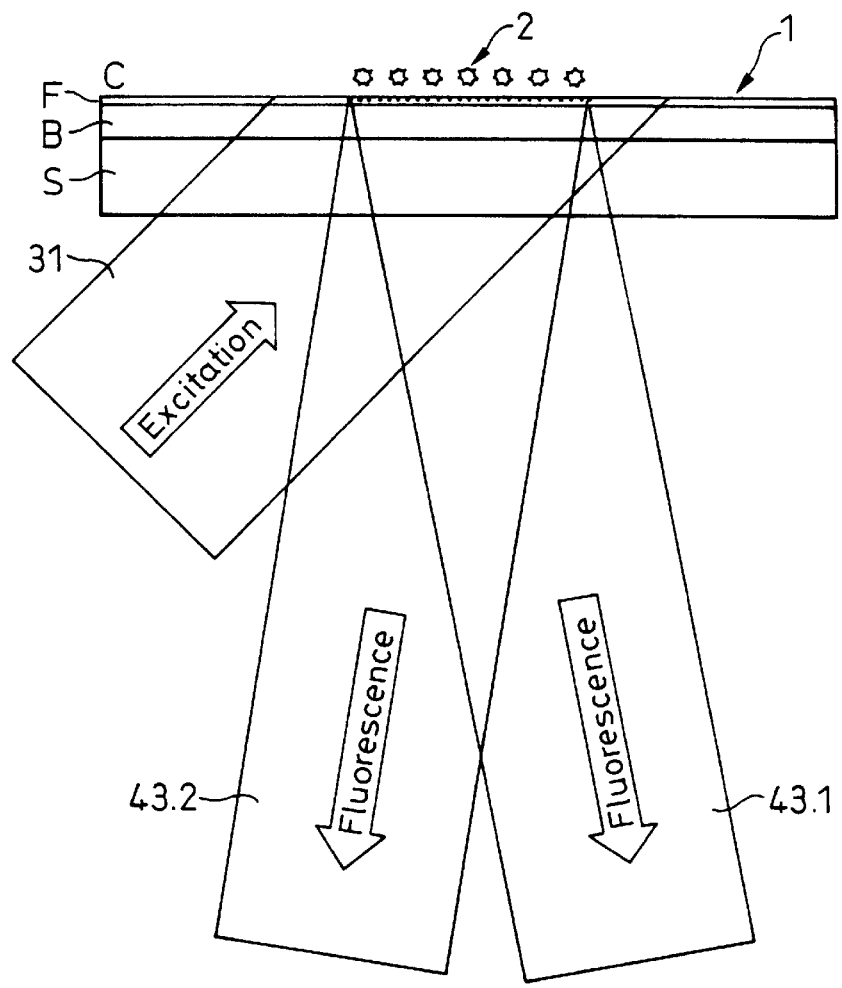
(b)
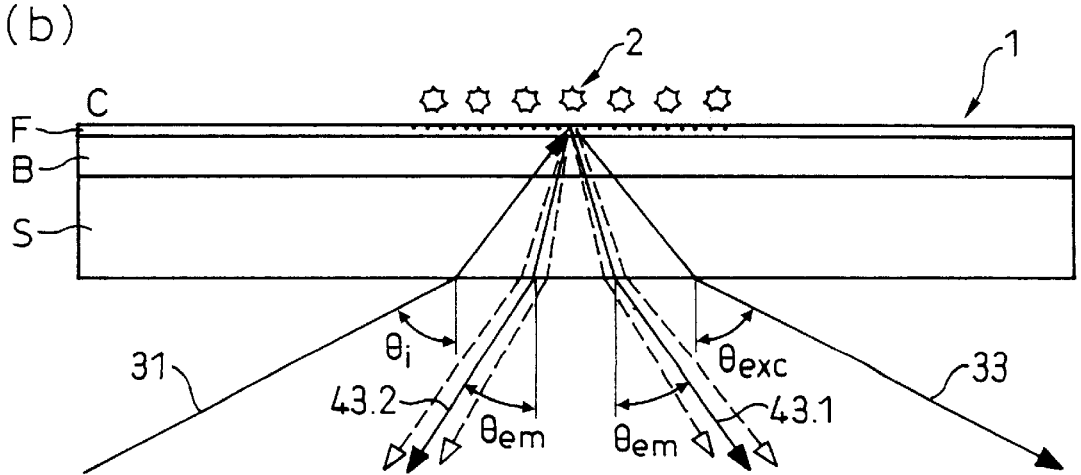

Fig. 4
(a)
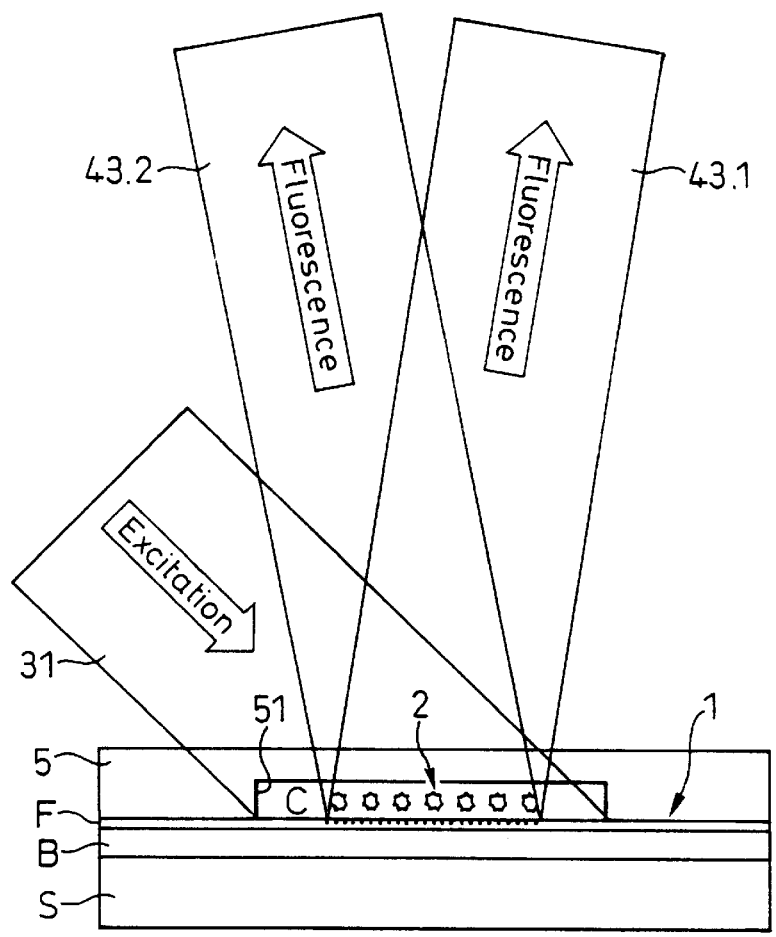
(b)
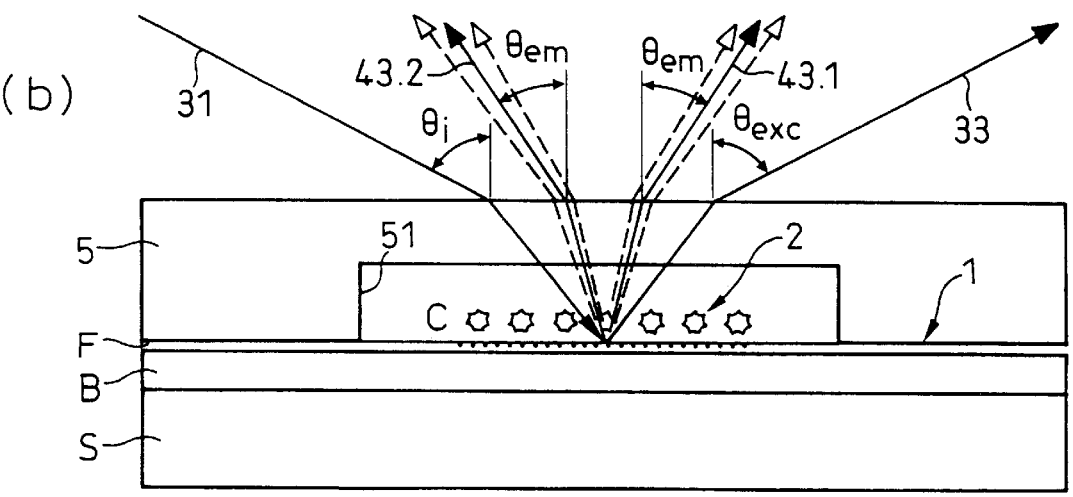

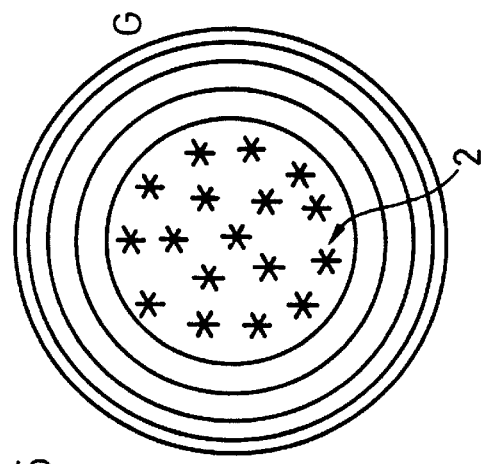
Fig.15
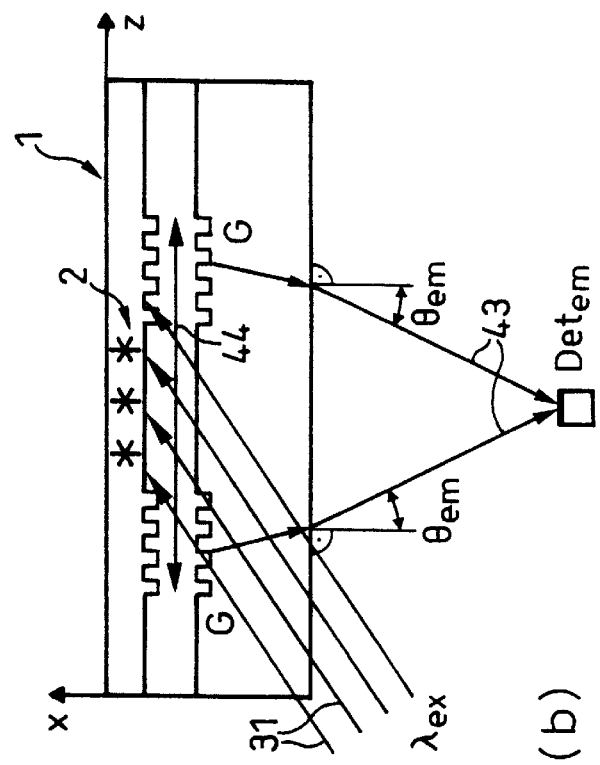
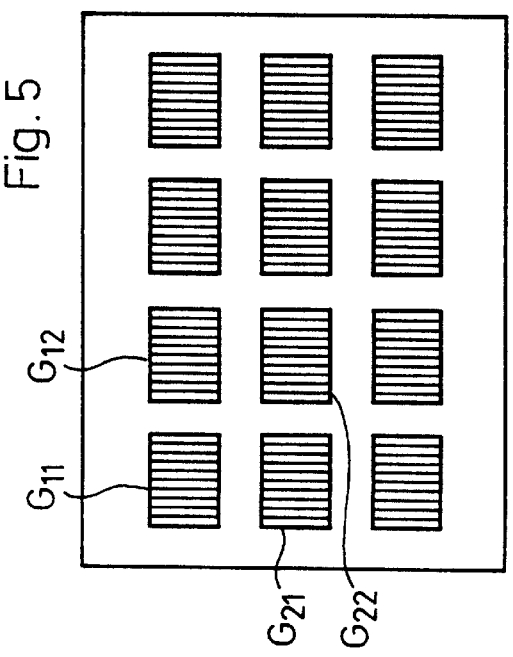
Fig.5

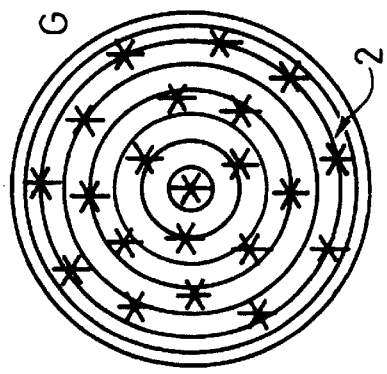
Fig.11 (a)
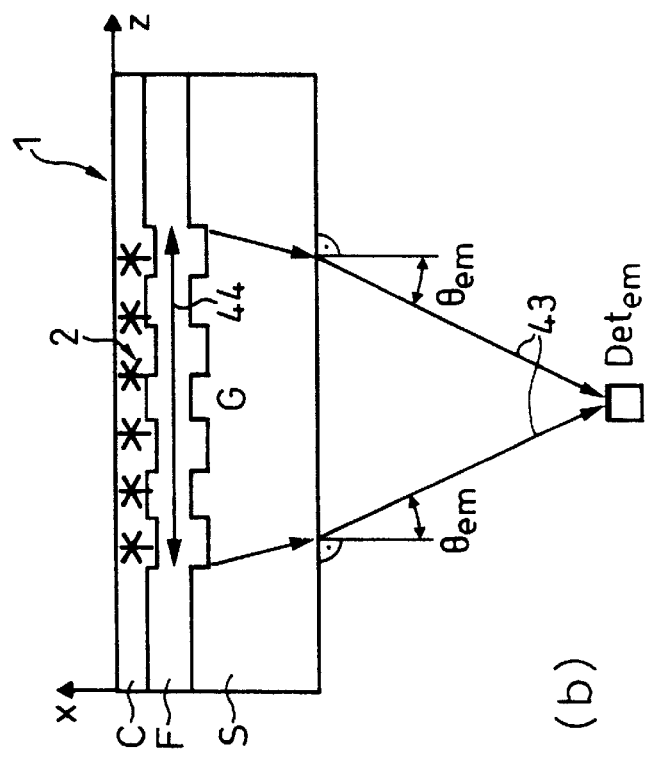
(b)
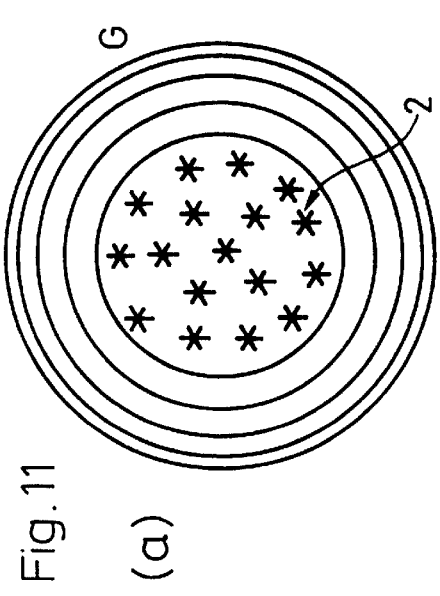
Fig.12 (a)
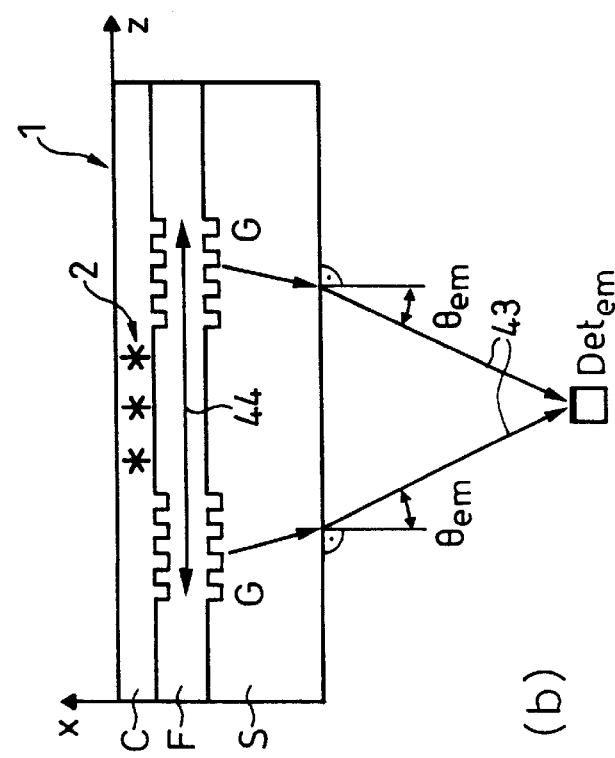
(b)

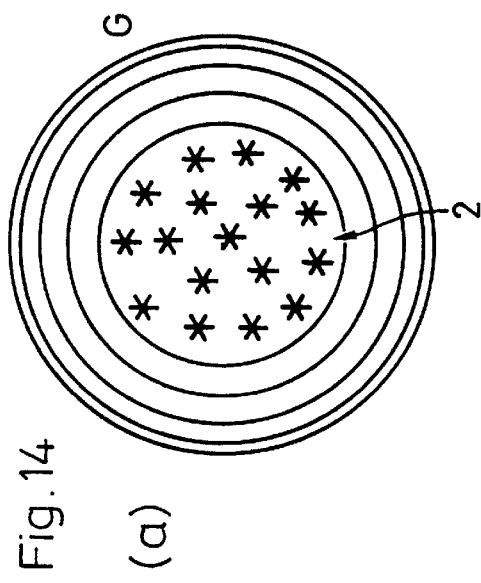
Fig.13
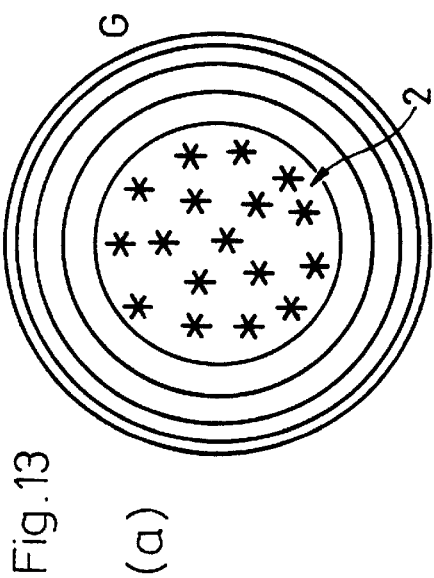
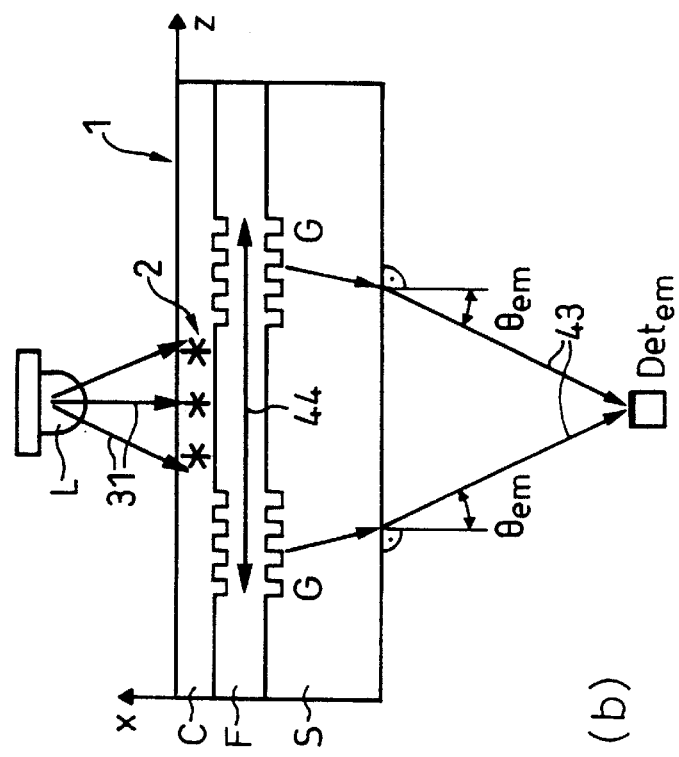
Fig.14

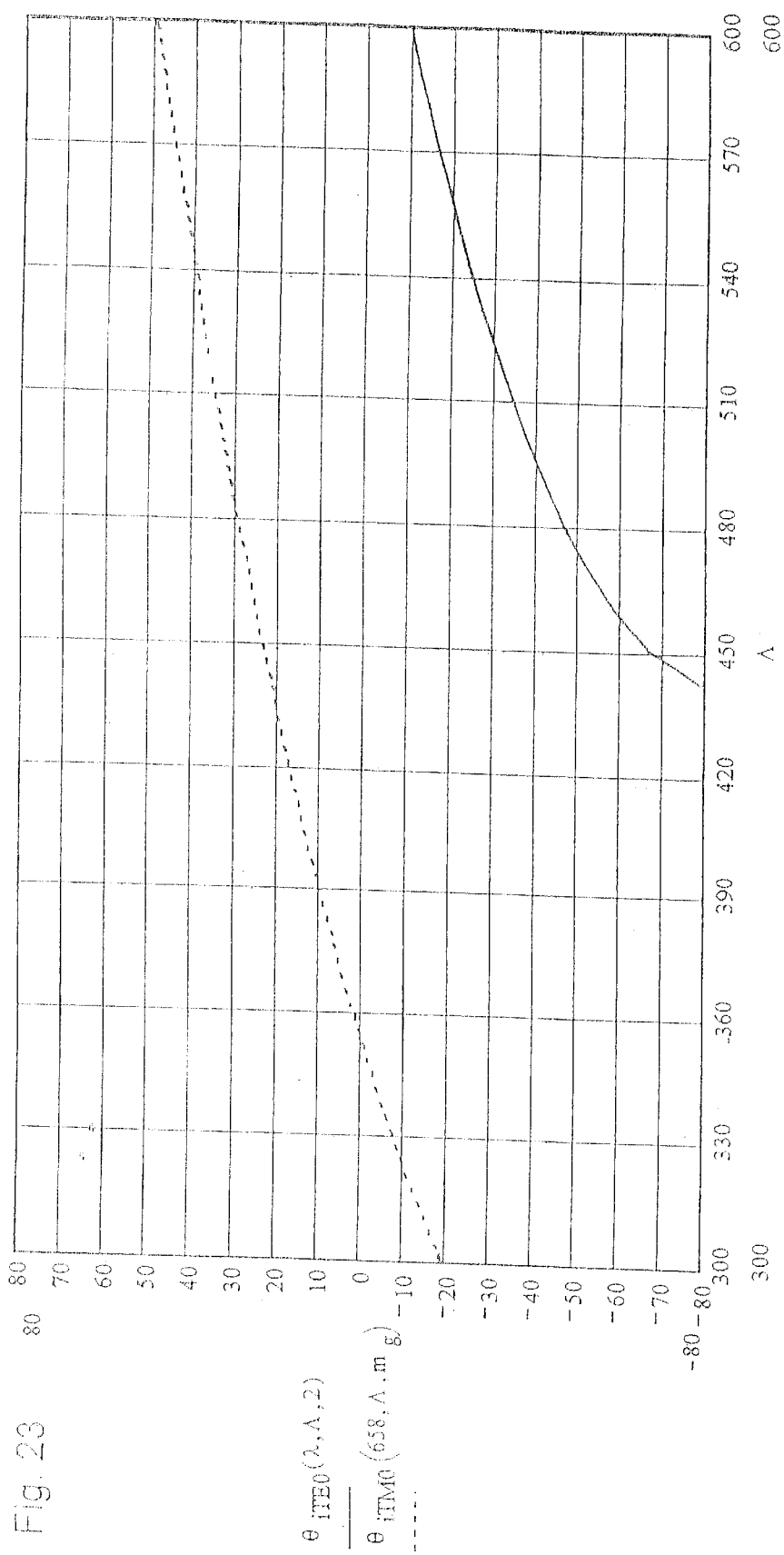

INTEGRATED-OPTICAL CHEMICAL AND BIOCHEMICAL SENSOR

BACKGROUND OF THE INVENTION

1. Field of the Invention

This invention relates to an integrated-optical chemical and/or biochemical sensor and to a method for integrated-optically sensing a chemical and/or biochemical substance.

2. Description of Related Art

Many present and upcoming applications of biochemical microsystems, especially for application areas such as medical, food and environmental, require the detection of several analytes being simultaneously present in a liquid.

One well-known and advantageous type of detection is optical. Among optical sensors, an important class are integrated optical (IO) sensors comprising a chip with a waveguide and sensing biolayers. Examples of IO biosensors are given in WO 92/19976 (CSEM); R.E. Kunz, "Totally Integrated Optical Measuring Sensors," Proc. SPIE, Vol. 1587, 98–113 (1992); WO 96/35940 (Ciba-Geigy).

Different sensing principles are being used. This invention deals with a subclass of sensors based on amplitude effects, i.e. those where the amplitudes of light waves (guided or/and freely propagating) are changed by the effect to be measured. Examples are luminescence (e.g. fluorescence, (electro-)chemo-luminescence), absorption or scattering (e.g. elastic and Raman).

The state-of-the-art procedure is to use two grating couplers (one input and a separate output). The publication EP-A-1,031,828 concerns a referencing scheme, which is also applicable for the new schemes disclosed here.

Drawbacks and problems of the state-of-the-art solutions are that they require too much of chip area, leading to very big chips and also to a small ratio between active and passive area. It also needs too much of (bio-)chemical area, since this is not efficiently used. Another problem with presently known array detection schemes is that the efficiency of on-chip referencing is limited by the large distance between sensing and referencing pads.

Sensing (signal) and referencing pads are both denoted by the term "measuring pad" in this document.

SUMMARY OF THE INVENTION

This invention aims at removing the drawbacks of the state-of-the art solutions for achieving amplitude-based high-density array sensors by reducing the area required for performing the sensing task, especially by reducing the area required by a single measuring pad in an array, and by increasing the ratio between active and passive chip area.

It is a further object of the invention to provide an IO sensor with:
  more efficient on-chip referencing
  chip and system miniaturization, i.e., more sensing pads per chip area (in the case of a two-dimensional sensor) or per volume (in the case of a three-dimensional sensor)
  less chemicals needed for chip biocoating
  less analyte volume needed due to reduced chip area for performing same task.

To take full advantage for practical applications, the following constraints shall be taken into account:
  the sensitivity is maintained or increased with respect to the conventional solutions; and
  the dynamic range is maintained or increased with respect to the conventional solutions.

This goal is achieved by realizing one or a combination of the following inventive measures:
  increasing the functionality of the measuring pads;
  adapting the measuring pad geometry to the sensing principle, to the overall chip geometry, and to the application;
  enhancing the efficiency of light collection (in general: "optical transfer processes");
  reducing the crosstalk between individual measuring pads by more efficient and more localized "light extraction" and/or by means of the geometry of the measuring pads.

The integrated-optical chemical and/or biochemical sensor according to the invention comprises
  a resonant waveguide structure;
  means for at least temporarily depositing a chemical and/or biochemical substance to be sensed on a surface of the resonant waveguide structure;
  means for irradiating the substance with electromagnetic radiation, making use of a first set of degrees of freedom;
  means for coupling out electromagnetic radiation from the resonant waveguide structure, making use of a second set of degrees of freedom which differs from the first set of degrees of freedom in at least one degree of freedom; and
  means for detecting electromagnetic radiation exiting from the resonant waveguide structure.

The irradiating means and/or the outcoupling means preferably comprise grating structures. The first and second set of degrees of freedom preferably comprises the diffraction order, the polarization, the guided-mode order, the grating vector and/or the planes of incidence and emergence.

The method according to the invention for integrated-optically sensing a chemical and/or biochemical substance using a resonant waveguide structure comprises the steps of
  irradiating the substance with first electromagnetic radiation, thereby using a first set of degrees of freedom;
  causing the substance to interact with the first electromagnetic radiation in such a way that it emits second electromagnetic radiation which differs in at least one parameter from the first electromagnetic radiation;
  causing the second electromagnetic radiation to excite a resonant electromagnetic field in the resonant waveguide structure;
  coupling electromagnetic radiation out from the resonant waveguide structure, thereby using a second set of degrees of freedom which differs from the first set of degrees of freedom in at least one degree of freedom; and
  detecting electromagnetic radiation exiting from the resonant waveguide structure.

The interaction of the substance with the first electromagnetic radiation preferably comprises luminescence, scattering, absorption, chemiluminescence and/or electrochemi-luminescence. The first and second set of degrees of freedom preferably comprises the diffraction order, the polarization, the guided-mode order, the grating vector and/or the planes of incidence and emergence.

Hence, a much higher density of sensing pads results for single-chip sensors, leading to several advantages as is described below. An important improvement is achieved for on-chip referencing, which is eased due to the smaller distance between measuring pads, and because multiple referencing pads can be used per sensing pad, e.g. one on top and one below or left and right or distributed around etc. This is especially important for sensors with very high sensitivities, since they are more affected by unspecific effects such as temperature and signal drift due to chemical and physical fluctuations.

The sensor according to the invention can be combined with known integrated-optical sensors based on other principles such as refractometry, for example using an integrated-optical light pointer (see, e.g., R.E. Kunz, "Miniature integrated optical modules for chemical and biochemical sensing", Sensors and Actuators B 38–39 (1997) 13–28).

BRIEF DESCRIPTION OF THE DRAWINGS

The invention is described in greater detail hereinafter relative to the attached schematic drawings.

FIGS. 1 and 2 show fluorescence-based sensors; (a) top view, (b) side view.

FIGS. 3 and 4 show further fluorescence-based sensors in a side view; (a) schematic of the sensor principle, (b) traces of the rays.

FIG. 5 shows an arrangement of a multisensor according to the invention.

FIGS. 11–15 show sensors according to the invention with circular gratings; (a) top view, (b) side view.

FIGS. 19–23 show calculations for angles of emergence vs. periodicity of the waveguide grating.

DETAILED DESCRIPTION OF THE INVENTION

Figure 6:
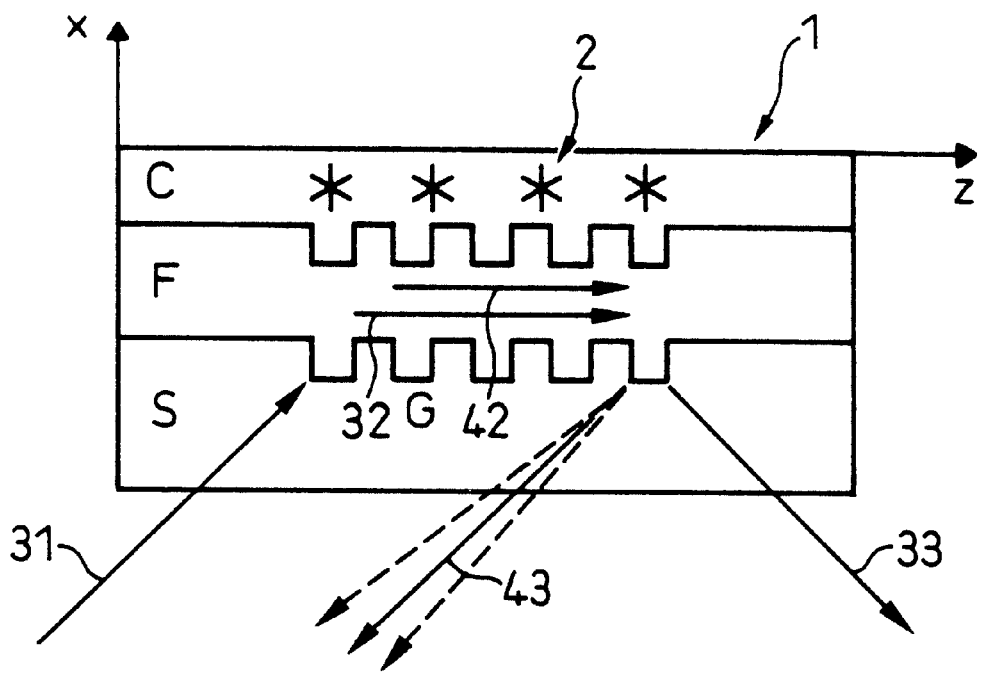
FIGS. 6–8 show sensors according to the invention in a side view.

A fluorescence-based sensor is depicted in FIG. 1, where (a) is a top view and (b) is a side view or a cross-section. The sensor comprises a waveguide 1 with a substrate S, e.g., made of plastic or glass material, and a waveguiding film F, e.g., made of $TiO_2$. The waveguide 1 is at least partially covered by a cover medium (or a sensing medium) C. A light source L, e.g., a laser, emits light 31 which is directed towards the sensor. A first grating coupler $G_1$ on or in the waveguide 1 is used to couple the incident light wave $u_i$, 31, into the waveguide 1 under an incoupling angle $\theta_i$. Light 32 guided in the waveguide 1 excites the fluorescence of molecules 2 to be measured, deposited on a surface of the waveguide 1. Fluorescent (emitted) light 42 is, at least partially, also guided in the waveguide 1 and then coupled out by means of a second grating coupler $G_2$ as a light wave $u_{em}$, 43, under an outcoupling angle $\theta_{em}$, whereas the exciting light is coupled out as a light wave $u_{ex}$, 33, under a different outcoupling angle $\theta_{ex}$; in the example of FIG. 1, $\theta_{em}<\theta_{ex}$. The light waves $u_{em}$, $u_{ex}$, i.e., their intensities and/or their local intensity distributions, are detected by means of detectors $Det_{em}$, $Det_{ex}$, respectively. The sensor according to FIG. 1 does not show the features defined in the claims and has the following drawbacks:

A large area is needed for the two gratings $G_1$, $G_2$ and the deposition area in between.

The efficiency is low because a part 44 of the fluorescent light propagates nearly in y direction and does not reach the outcoupling grating $G_2$.

There might be undesired crosstalk between the two signals measured by the detectors $Det_{em}$, $Det_{ex}$ because the outcoupling angles $\theta_{em}$, $\theta_{ex}$ of the emitted light 43 and the exciting light 33 differ only by a small difference angle of typically $\theta_{ex}-\theta_{em}<5°$ and are therefore not clearly separable from each other. In other words, the signal-to-noise ratio is low.

FIG. 2 shows an improved sensor where the molecules 2 to be measured are placed directly on the grating coupler G, and the readout is also performed by the same grating G. This sensor requires a smaller area than the arrangement of FIG. 1. The efficiency is higher than with the arrangement of FIG. 1. However, the crosstalk problem remains the same if the measures according to the invention are not applied.

The arrangement of FIG. 3 is similar to that of FIG. 2, but the fluorescent light is coupled out in two symmetric output diffraction orders 43.1 and 43.2, e.g., in the $+1^{st}$ and in the $-1^{st}$ order, respectively. By choosing the grating period of the grating G appropriately, it is possible to merge the two fluorescent beams 43.1, 43.2. The fluorescent light 43.1, 43.2 typically does not show one single well-defined wavelength, but rather a certain wavelength distribution depending on the characteristics of the fluorescent molecules. Therefore, the fluorescent light 43.1, 43.2 is coupled out under a certain distribution of angles of emergence, which is sketched by dashed lines. Another reason for the spreading of the outcoupled light 43.1, 43.2 is scattering, mainly in the region of the molecules 2.

In the arrangement of FIG. 4, the light path is on the side of the molecules 2, whereas in the arrangement of FIG. 3, it is on the side of the substrate S. Therefore, the substrate S may be opaque in the case of FIG. 4. The sensing region G is preferably covered by cover means 5, e.g., made of plastic material, in which a recess or a channel 51 for the sensing region G is formed.

FIG. 5 shows an arrangement of a multisensor. Each grating pad $G_{11}$, $G_{12}$, ..., $G_{21}$, $G_{22}$, ... corresponds to a measurement zone. The reading of a multisensor of this type can be made in parallel (one collimated beam, one wavelength imaging of the surface on a camera) or sequentially. In the latter case there are at least two possibilities: i) a small collimated (or slightly focused) beam moved from one grating pad to the other, or ii) a large collimated beam and different grating period for each pad; the sequential reading can be made either by changing the coupling angle or by changing the wavelength of the incident light.

The sensors shown in FIGS. 1–5 may be conventional fluorescence sensors, or they may show the features according to the invention. These features are explained in detail in the following figures. For reasons of clarity, some features already introduced in FIGS. 1–5, such as the light source L, are not shown in the following figures.

One measuring pad of the sensor according to the invention preferably comprises one single grating G on or in a waveguide structure 1, as shown in FIG. 6. Molecules 2 to be sensed are deposited on the grating G. The grating G is irradiated by an incident light beam 31, e.g., a laser beam, which is coupled into the waveguide structure 1 by the grating G using a first diffraction order, e.g., $m_{g,ex}=1$. The incident guided light 32 interacts with the fluorescent molecules 2, which emit light 42 of a longer wavelength. A part of the emitted light 42 excites a resonant electromagnetic field in the waveguide structure 1 and is coupled out from the waveguide structure 1 by the grating G. According to a first aspect of the invention, emitted light 43 is coupled out using a second diffraction order, e.g., $m_{g,em}=2$, which differs from the first diffraction order $m_{g,ex}$. By this measure, the emitted outcoupled light 43 is clearly separated from exciting light 33 which is reflected ($m_{g,ex}=0$) and/or coupled out using the first diffraction order $m_{g,ex}=1$. "Clearly separated" means in this document separated in such a way that it can be detected without any special measures; for practical purposes, a "clear separation" is achieved if the angles of emergence differ by at least about 5°. Emitted light (not shown) and exciting light 33 coupled out in the first diffraction order $m_{g,ex}=1$, $m_{g,em}=1$ are not clearly separated; moreover, light coupled out using the first order is superimposed by scattered light (not shown). There is also exciting light (not shown) coupled out using the second diffraction order $m_{g,ex}=2$; however, this does not disturb too much because its intensity is lower. The dashed lines indicate that fluorescent light 43 is coupled out under a certain distribution of angles of emergence. Of course, other diffraction orders may be used; for instance, incident light may be coupled in using a first diffraction order $m_{g,ex}=2$ and emitted light may be coupled out using a second diffraction order $m_{g,em}=\pm 1$. A clear separation increases the signal-to-noise ratio.

Figure 7:
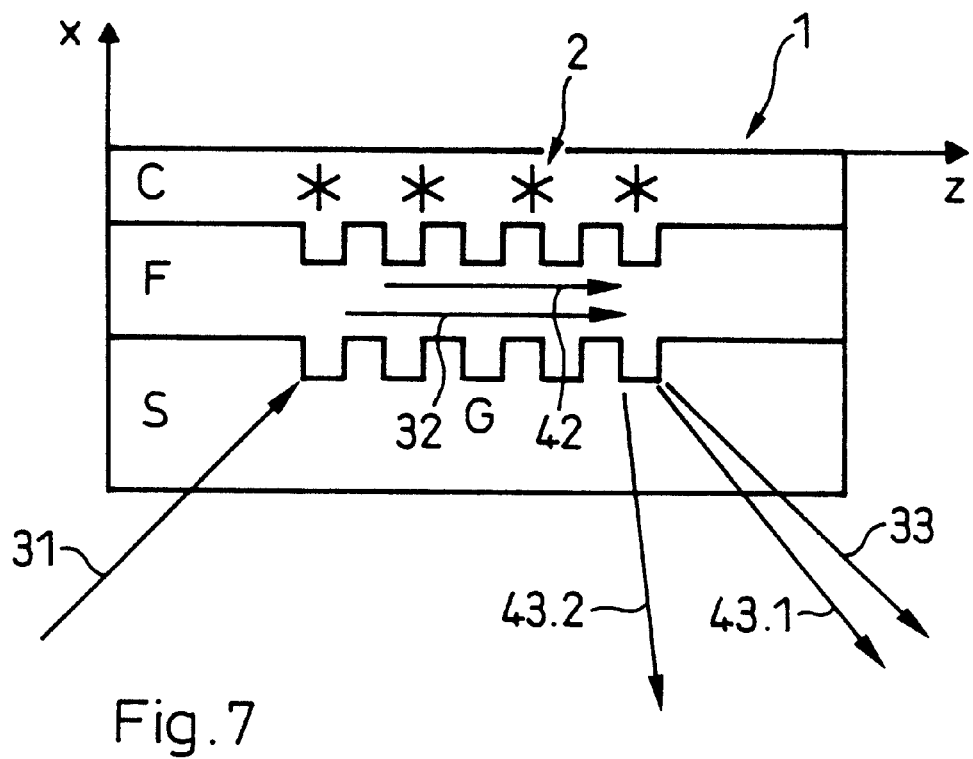

According to a second aspect of the invention, emitted light 43.2 having a polarization which differs from the polarization of the exciting light 33 is coupled out of the waveguide structure 1, as shown in FIG. 7. This is possible because during the process of fluorescence, polarization is not necessarily maintained. The diffraction order may be the same as or other than that of the incident light 31. As long as the polarization is different, the emitted light 43.2 can clearly be separated from other light 33. There may also be emitted light 43.1 coupled out with the same polarization as the exciting light 31, 33, which may not be clearly separated from the outcoupled exciting light 33.

Figure 8:
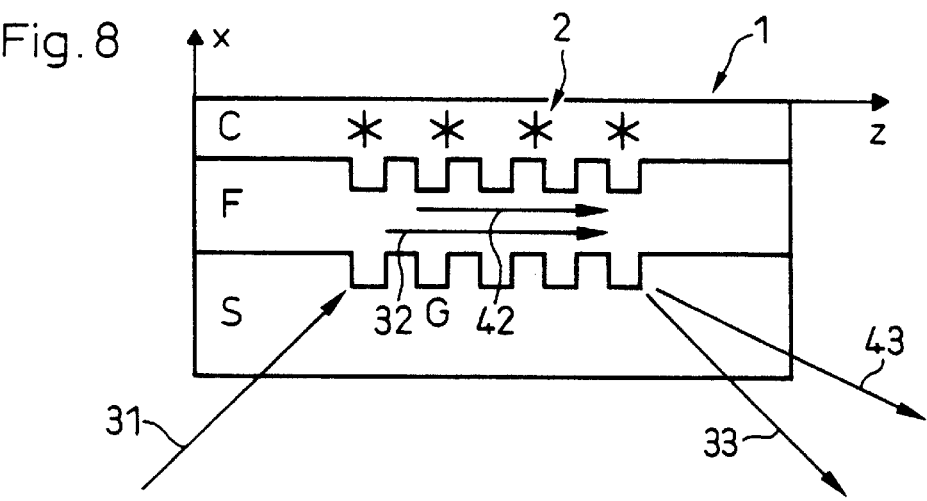

In the embodiment of FIG. 8, the incident light 31 excites a guided wave 32 in the waveguide which has a first mode order, e.g., $m_{ex}=0$. According to a third aspect of the invention, a guided wave 42 having a second mode order, e.g., $m_{em}=1$, which differs from the mode order of the exciting light 32 is coupled out of the waveguide structure 1. The diffraction order and the polarization may be the same as or other than that of the outcoupled exciting light 33; in any case, the two outcoupled light components 43, 33 will be clearly separated.

Figure 9:
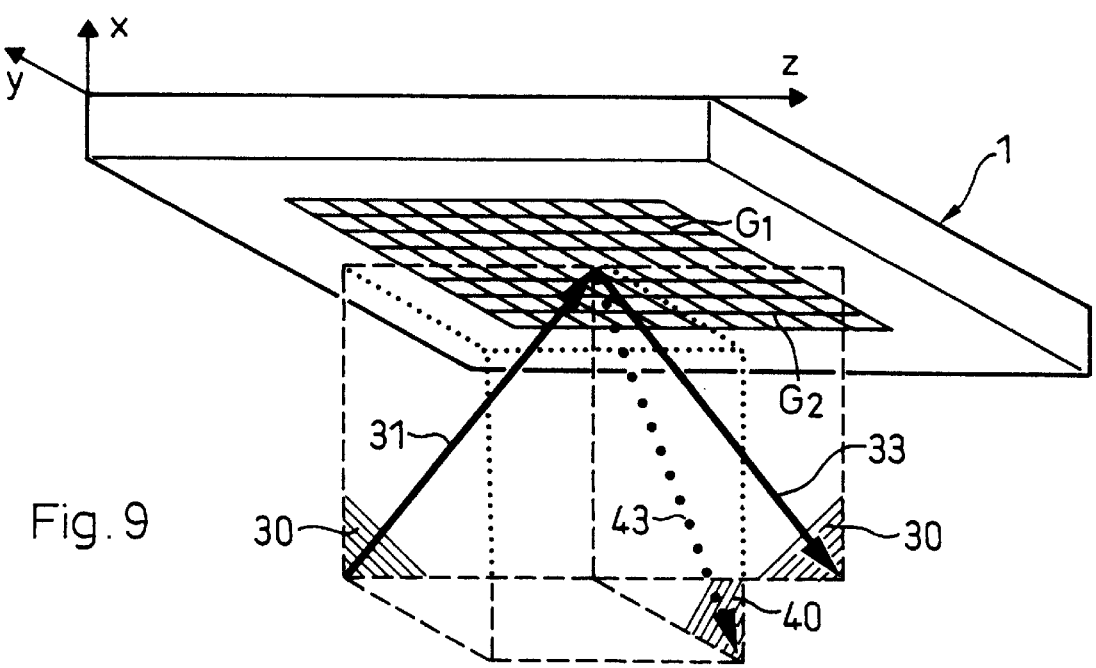
FIG. 9 shows a further sensor according to the invention in a three-dimensional view.
Figure 10:
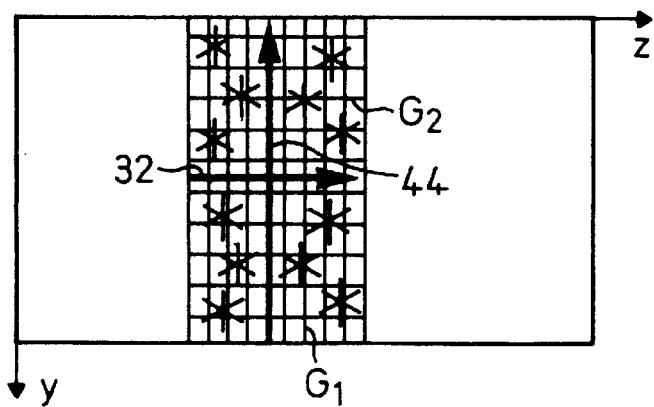
FIG. 10 shows the sensor of FIG. 9 in a top view.

FIGS. 9 and 10 show a fourth embodiment of a sensor according to the invention. It comprises a grating coupler composed of two superposed subgratings $G_1$, $G_2$. The first subgrating $G_1$ has a grating vector in z direction, i.e., lines parallel to the y direction, and is used for incoupling the exciting light 31. The second subgrating $G_2$ is perpendicular to the first subgrating and is used for outcoupling emitted light 44. This is possible because there is emitted light 44 with components in y (or -y) direction (cf. FIG. 1). As can be seen from FIG. 9, the outcoupled emitted light 43 does not propagate in the same first plane 30 as the incident light 31 and the outcoupled exciting light 33, but in a second plane 40 which is perpendicular to the first plane 30. With this arrangement, it is possible to very efficiently separate outcoupled emitted light 43 from outcoupled exciting light 33, thus increasing the signal-to-noise ratio.

The sensor of FIG. 11 uses a circular (and possibly focusing) grating G to collect the fluorescent light 44 more efficiently, thus reducing the area of biocoated surface and crosstalk between different measuring pads $G_{11}$, $G_{12}$, ..., $G_{21}$, $G_{22}$, ... of a multisensor (cf. FIG. 5). In the arrangement of FIG. 12, the molecules 2 are directly placed on a circular grating coupler pad G.

FIG. 13 shows (non-resonant or partially resonant) excitation with a broadband light source L, e.g., a light-emitting diode (LED).

FIGS. 14 and 15 show embodiments of the optical arrangement with further possibilities of non-resonantly or partially resonantly exciting fluorescence. In the embodiment of FIG. 14, the exciting light 31 shows a certain angular range or distribution and is reflected by a mirror M through the substrate S and the waveguiding film F onto the sensing pad. In the embodiment of FIG. 15, the exciting light 31 comes in through the substrate S and the waveguiding film F from essentially one direction.

Figure 16:
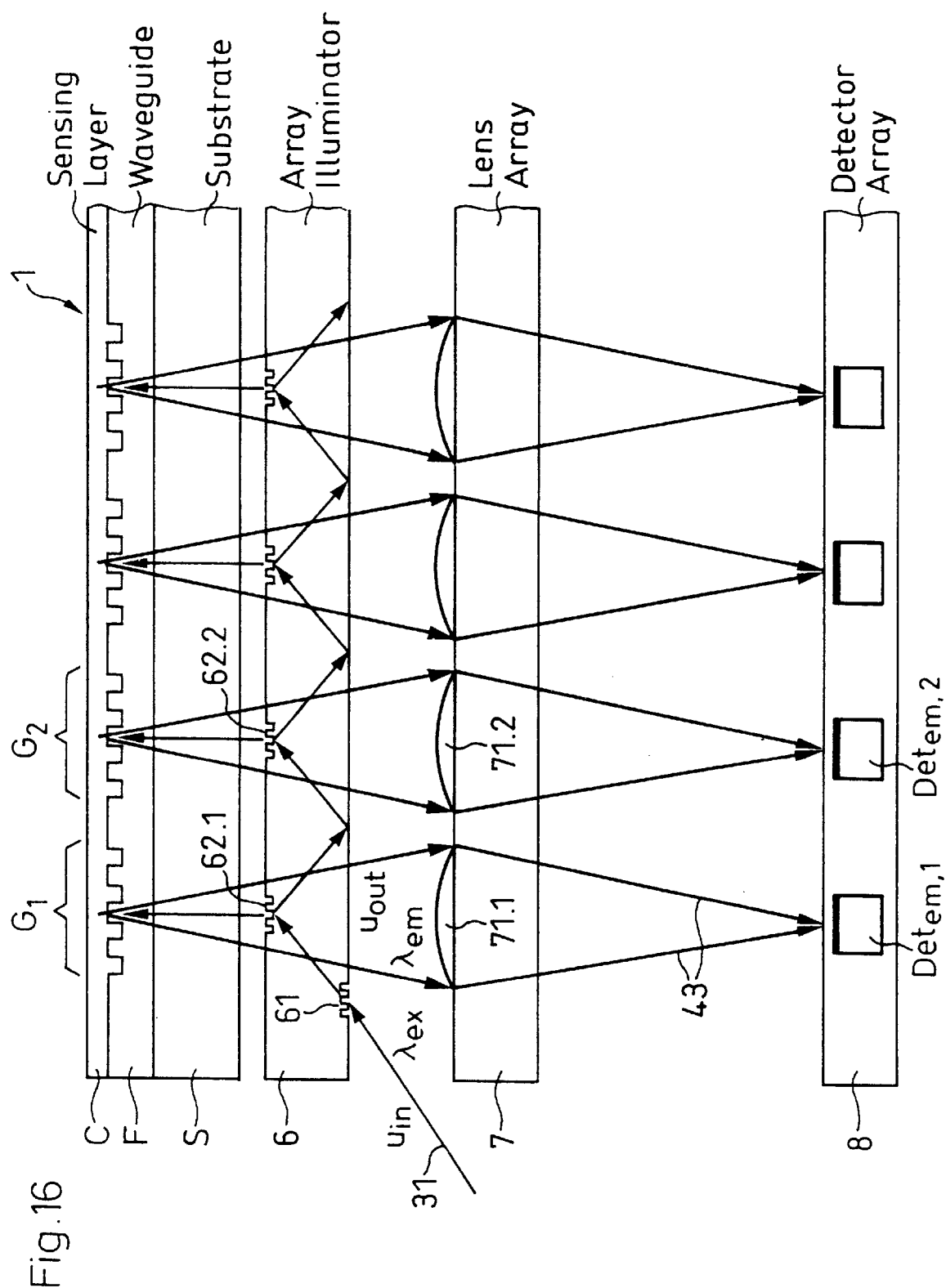
FIG. 16 shows an example of a complete sensor system optical layout.

FIG. 16 shows a (one-or two-dimensional) detector array according to the invention. The example shown is a fluorescence parallel readout sensor. The illumination of the sensing layer C on the surface of a first waveguide 1 occurs directly via first order incoupling or in a non-resonant way from an array illuminator 6. The array illuminator 6 may consist of a second waveguide (or light guide) with an input grating coupler 61 for coupling in incident light $u_{in}$, 31, and a plurality of partial output grating couplers 62.1, 62.2, ... for coupling out a part of the guided light. Preferably, a partial output grating coupler in the second waveguide 6 corresponds to a grating coupler $G_1$, $G_2$, ... in the first waveguide 1. Each grating coupler $G_1$, $G_2$, ... in the first waveguide 1 is imaged onto a detector $Det_{em,1}$, $Det_{em,2}$, ... on a detector array 8 by a lens 71.1, 71.2, ... on a lens array 7. The detectors $Det_{em,1}$, $Det_{em,2}$, preferably detect the light intensity of the $\pm 1^{st}$ diffraction orders of the emitted outcoupled light 43.

In the following, a setup and results of a preliminary experiment showing the feasibility of the invention are described.

Figure 17:
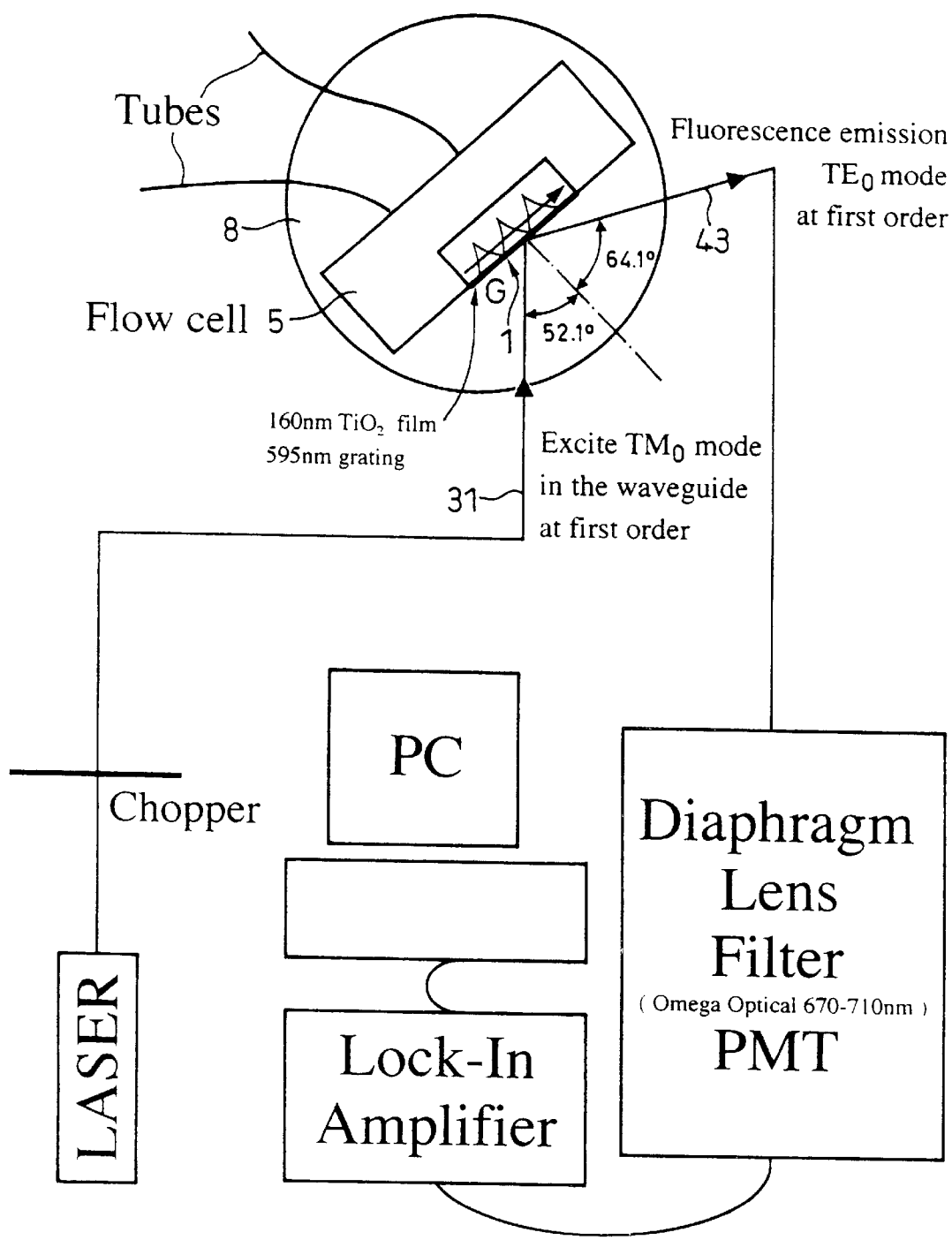
FIG. 17 shows a preliminary experimental setup for fluorescence measurements.

FIG. 17 shows the setup of this preliminary experiment. A replicated (hot-embossed) sensor chip was used. The sensor chip had a single grating coupler pad G measuring only 1×4 mm$^2$ for performing all the tasks of input coupling the incident exciting light 31, exciting the fluorescence, and extracting the emitted output light 43. The sensor chip comprised a 160 nm TiO$_2$ waveguide, being structured with a 1 mm wide grating G with a grating period of 595 nm. For immobilization of the sensing layer C, mouse IgG have been attached on the chip by photolinking. A flow cell 5 with the chip was mounted on a turntable 8. The grating pad G was illuminated with a 658.1 nm laser beam 31 at the coupling angle corresponding to the first order for a TM$_0$ mode. This beam excited the TM$_0$ mode in the waveguide 1. Then the detection system was adjusted to the outcoupling angle of a 690 nm TE$_0$ mode in its first order. The fluorescence of Cy-5 conjugated adsorbed donkey-anti-mouse-antibodies was measured via the TE$_0$ mode in the same waveguide 1.

Course of the experiment:
  Buffer measure background once a minute
  Shutter closed measure dark level
  Background stable switch valve to analyte
  Reagent excite for 5 seconds and measure signal
  Close shutter wait 1 minute
  Open shutter excite for 5 seconds and measure signal
  Repeat to saturation of signal Apply buffer and go ahead measuring once a minute.

General data and experimental parameters:

Chip: REK 980406 a M202 replicated (hot-embossed) in polycarbonate
$\Lambda$=595 nm
$h_g$=10 nm
$h_f$=160 nm $Ti_{O2}$ Laser (excitation): $\lambda$=658.1 nm Polarization (ex.): TM Coupling angle (ex.): +52.1°

Fluorescence Cy-5: $\lambda \geqq 670$ nm

Measured polarization: TE

Output angle (emission): 64.1°

Optical emission filter: Omega Optical (690±20) nm

Photomultiplier tube: Hamamatsu H6240-01

Amplification: Lock-in amplifier
  Bandpass filter Out
  Line In
  Line x2 In
  Offset Off
  Reference f, rectangular
  Time constants:
    Pre: 1 s
    Post: 1 s Buffer: PBS with BSA (1 mg/ml)

Sensing Layer: Mouse IgG applied on chip by photolinking

Reagent: $10^{-8}$ M Cy-5-conjugated donkey-anti-mouse-IgG

Setup:

Illumination angle: 52.1°

Measuring angle: 64.1°

Measuring area: ~4 mm²

Figure 18:
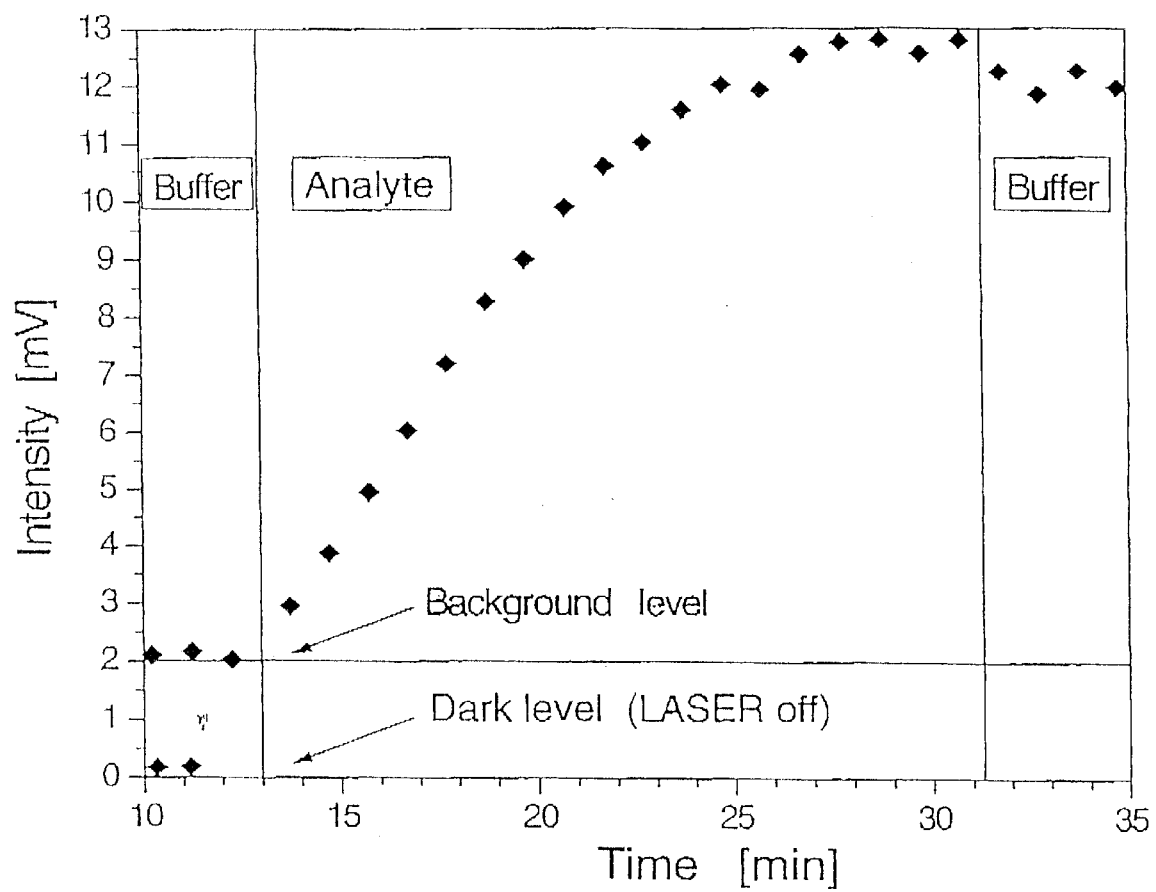
FIG. 18 shows the signal of one assay for the experiment of FIG. 17.

FIG. 18 shows the signal of one assay measured in this experiment. The curve starts at 10 minutes total time. By this time, everything was correctly prepared and adjusted. The first data points have been measured while buffer was flowing through the flow cell 5. This is the background level that originates from scattered laser light and from the volume fluorescence of the polycarbonate substrate S. The shutter blocking the laser was opened for 5 seconds once per minute. The level measured during the time the shutter was closed corresponds to the photomultiplier dark counts. At minute 13 the reagent, present in a concentration of $10^{-8}$ M in the same buffer solution, was applied to the flow cell. The rise of the sensor output signal between times 13 and 28 is due to the absorption of antibodies, conjugated with Cy-5, to the mouse-IgG layer on the chip surface. The intensity corresponds to the fluorescent light emitted by the Cy-5-label of these molecules into the $TE_0$ waveguide mode. After about 15 minutes (minute 28) the signal rise ended. This effect shows that the antibodies saturated the binding sites on the surface. The signal diminished a little after buffer was applied on the chip again (minute 31). This small decrease corresponds to the former contribution to the signal by those molecules which were only unspecifically absorbed and/or just present in the analyte volume in the region of the evanescent wave and non washed away.

FIGS. 19–23 show calculations illustrating the advantages of the sensor according to the invention. The following definitions are used:

| | |
|---|---|
| $n_a, n_s, n_f, n_l, n_c =$ | Refractive indices of Ambient, Substrate, waveguiding Film, sensing Layer, Cover medium |
| $h_f, h_l =$ | Thicknesses of waveguiding Film and sensing Layer |
| $\lambda =$ | Wavelength of light |
| $\lambda_{ex}, \lambda_{em} =$ | explicitely denoted wavelengths for exciting the luminescence and for the luminescent emission |
| $\Lambda =$ | Periodicity of waveguide grating |
| $G_1, G_2 =$ | Input coupler, Output coupler |
| $\theta_i =$ | Grating coupler resonance angles |
| $\theta_{ex}, \theta_{em} =$ | explicitely denoted angles for the excitation and emission wavelengths |
| $m_g$ | Grating diffraction order |
| $m =$ | Order of the waveguide mode |
| $TE_m, TM_m =$ | Transverse Electric and Transverse Magnetic modes. |

The calculations were performed with the following parameters:

| | |
|---|---|
| $n_a =$ | 1.00 |
| $n_s =$ | 1.58 |
| $n_f =$ | 2.39 |
| $n_l =$ | 1.45 |
| $h_f =$ | 150 nm |
| $h_l =$ | 10 nm |
| $\lambda_{ex} =$ | 658 nm (commercial laser diode) |
| $\lambda_{em} =$ | 670 nm (Cy5 fluorescent labels) |
| $\Lambda =$ | Abscissa (300 . . . 600 nm). |

Figure 19:
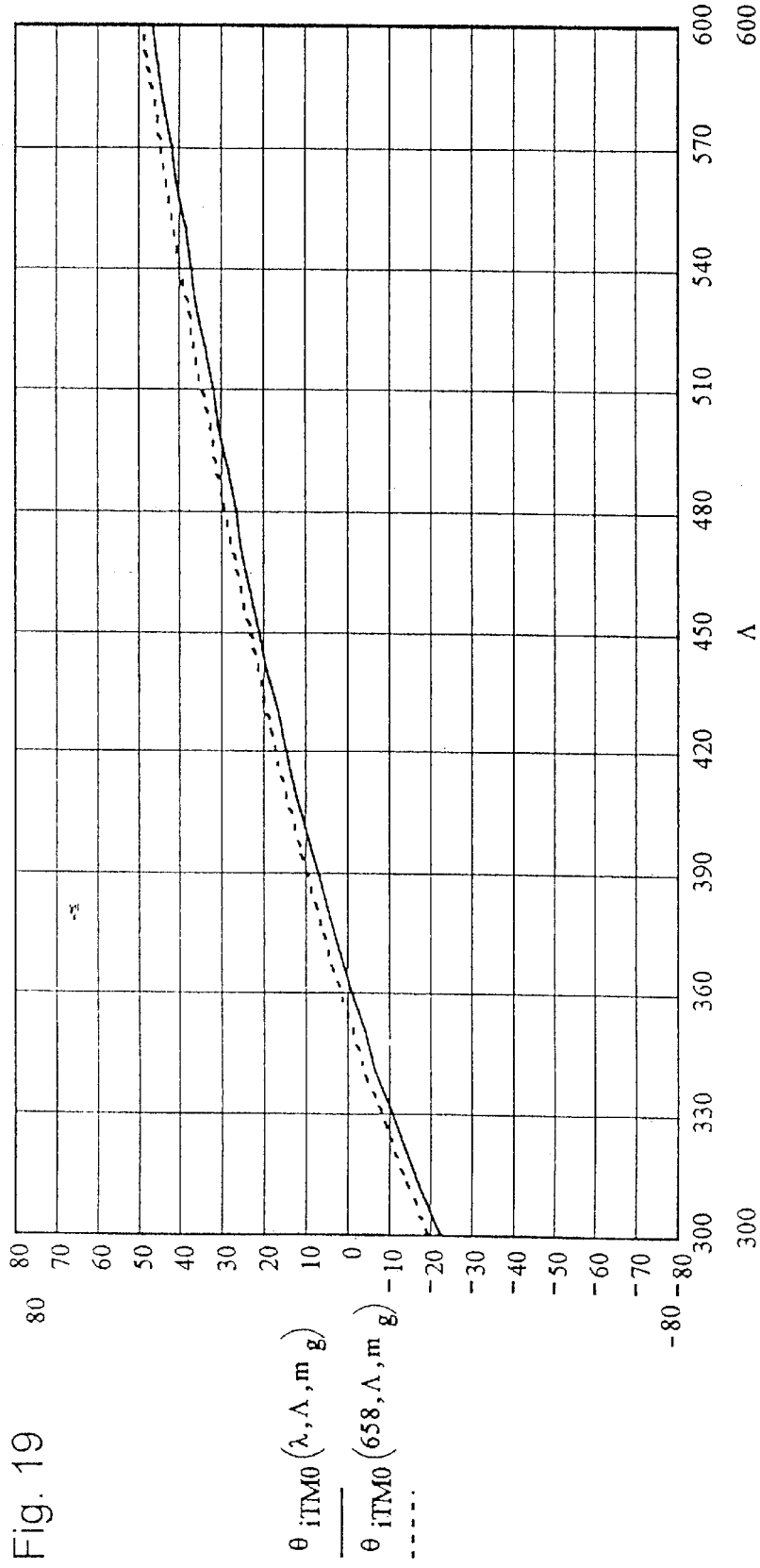

FIG. 19 shows the excitation (dashed line) and emission (solid line) angles (in degrees) for a conventional waveguide sensor using
  the same polarization (TM)
  the same mode order (m=0)
  at the same grating diffraction order ($m_g$=1)
both for the excitation of the luminescence and for observing the emitted luminescent radiation.

Due to the fact that the same degrees of freedom are used for input and output, the angular separation between the background contribution and the signal (emitted radiation, in this example at $\lambda$=670 nm) is in the order of 3°.

Figure 20:
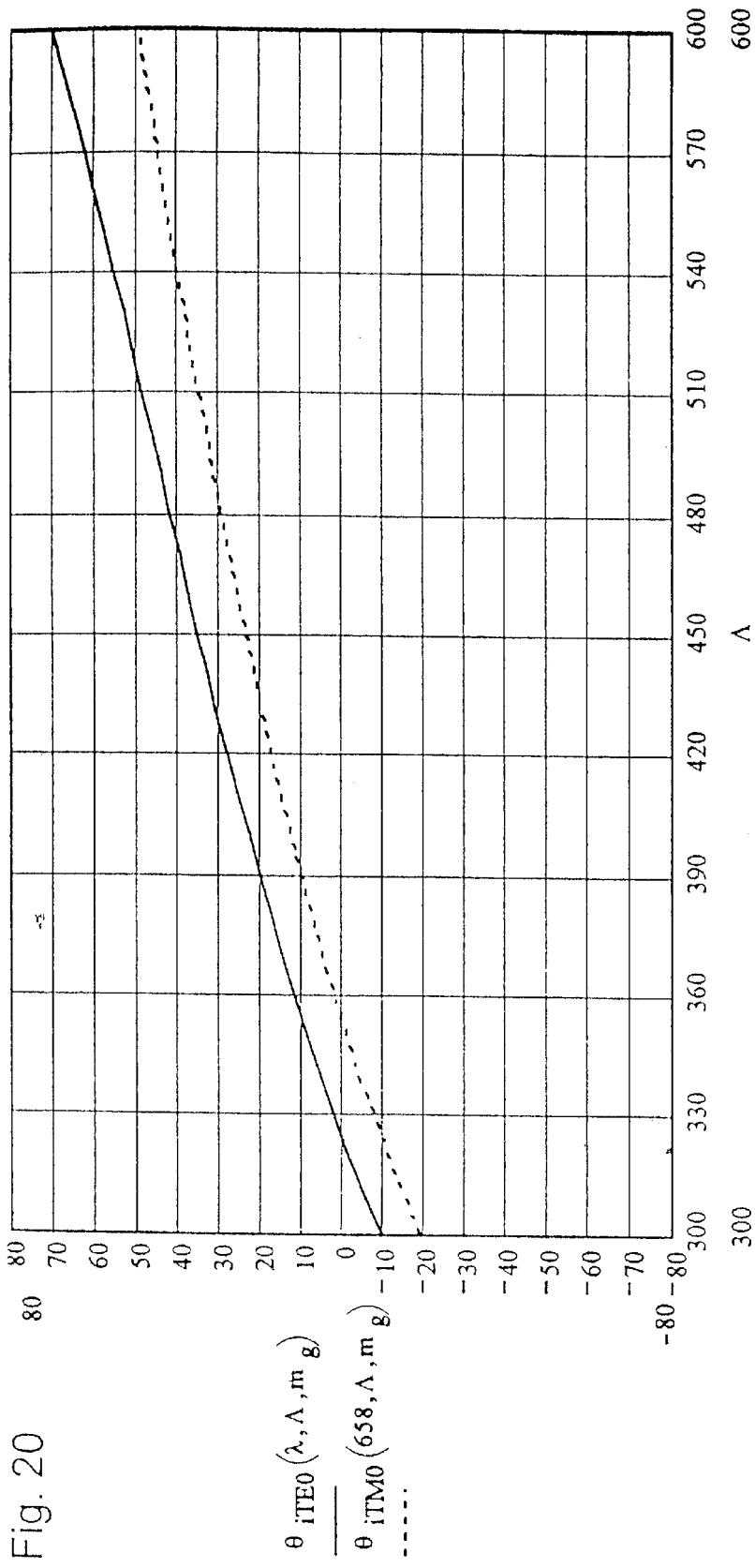

FIG. 20 shows the excitation (dashed line) and emission (solid line) angles (in degrees) for a waveguide sensor according to the invention using
  the same mode order (m=0)
  at the same grating diffraction order ($m_g$=1)
but different polarizations (TM for excitation, TE for observing the luminescent emission).

Making use of different polarizations for input and output gives rise to a significant increase of the angular separation between the excitation and emission channels. In this example, the angular separation is larger than about 9°, and still leaves a great freedom for designing the absolute angles for optimizing readout; choosing a periodicity of 330 nm leads for instance to an output angle near 0° (i.e. normal to the surface). The separation can be further increased by choosing a greater periodicity, reaching values of more than 20° (e.g. at $\Lambda$>600 nm). An additional advantage of this approach is that the background suppression can be further enhanced by using polarization filters in the output channel.

Figure 21:
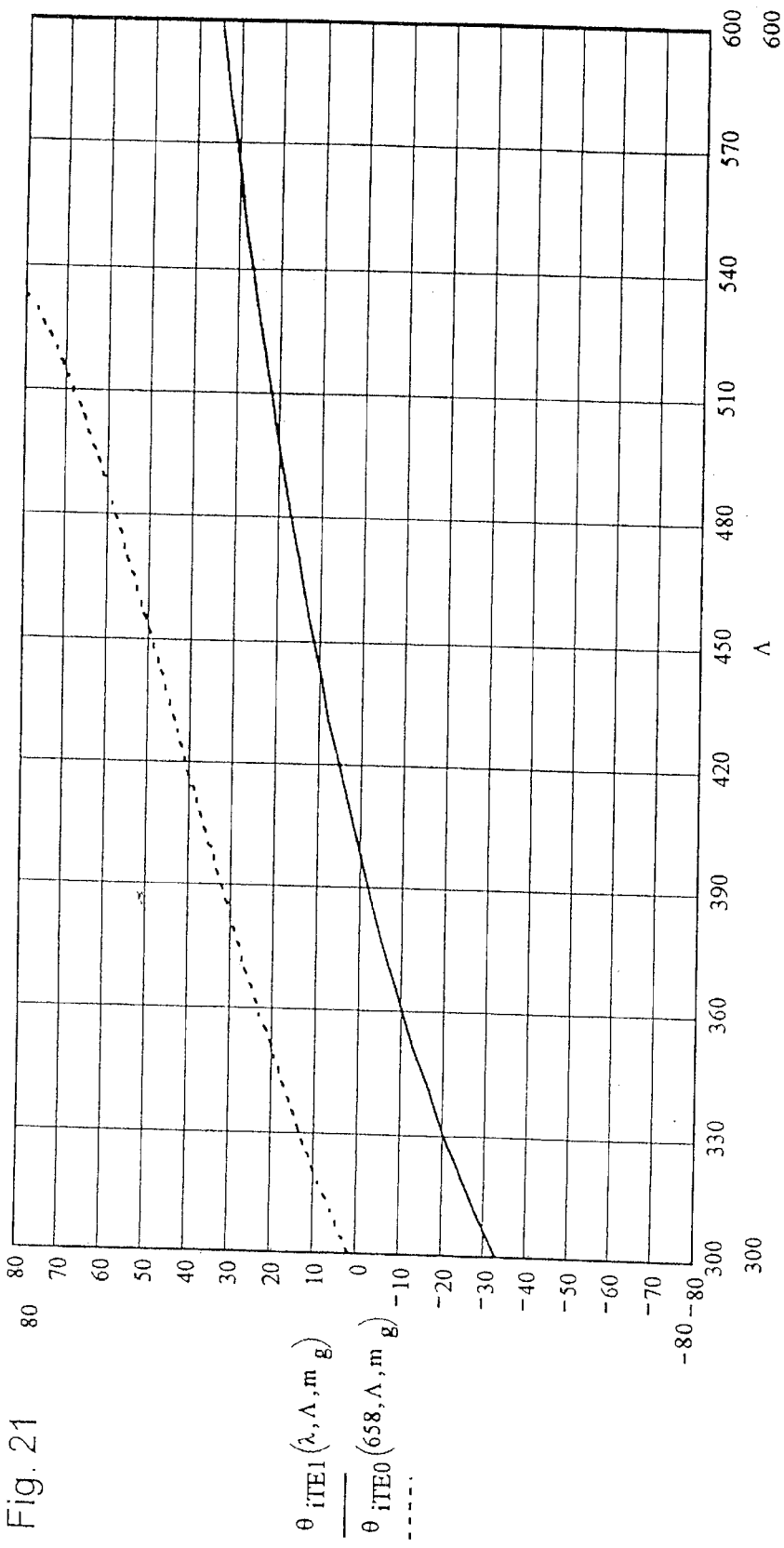

FIG. 21 shows the excitation (dashed line) and emission (solid line) angles (in degrees) for a waveguide sensor according to the invention using
  the same polarization (TE)
  at the same grating diffraction order ($m_g$=1)

but different mode orders (m=0 for excitation, m=1 for observing the luminescent emission).

Making use of different mode orders for input and output gives rise to a significant increase of the angular separation between the excitation and emission channels. In this example, the angular separation is larger than 30°, and still leaves a great freedom for designing the absolute angles for optimizing readout; choosing a periodicity of 400 nm leads for instance to an output angle near 0° (i.e. normal to the surface). The separation can be further increased by choosing a greater periodicity, reaching values of more than 40° (e.g. at Λ>480 nm).

Figure 22:
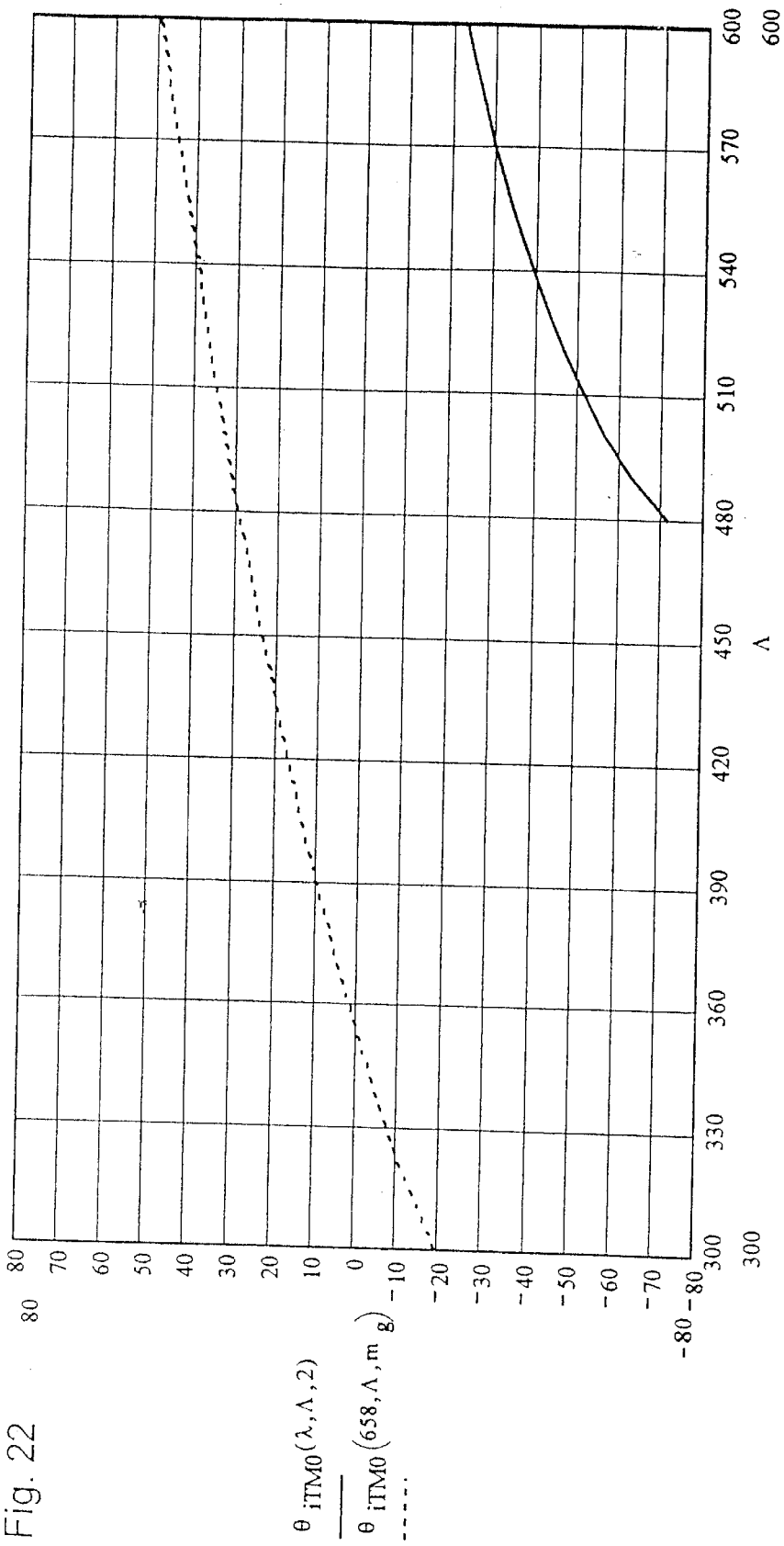

FIG. 22 shows the excitation (dashed line) and emission (solid line) angles (in degrees) for a waveguide sensor according to the invention using the same mode order (m=0) and the same polarization (TE)

but different diffraction orders ($m_g=1$ for excitation, $m_g=2$ for emission detection).

Making use of different diffraction orders for input and output gives rise to a significant increase of the angular separation between the excitation and emission channels. In this example, the angular separation is larger than 70°, however, the freedom for designing the absolute angles for optimizing readout is somewhat limited, but still allows low angles if large grating periodicities are chosen; choosing a periodicity of >600 nm leads for instance to output angles of a magnitude less than about 20° away from normal incidence. The separation can be further increased by choosing a periodicity in the vicinity of 580 nm, reaching values of about 100°.

FIG. 23 shows the excitation (dashed line) and emission (solid line) angles (in degrees) for a waveguide sensor according to the invention using the same mode order (m=0)

but different diffraction orders ($m_g=1$ for excitation, $m_g=2$ for emission detection) and different polarizations (TM for excitation, TE for observation of the emission).

Making use of changing more than one degree of freedom for input and output gives rise to a significant increase of the angular separation between the excitation and emission channels, and widens the parameter space for optimizing the optical readout arrangement. In this example, the angular separation is larger than 60°, and still allows low angles if large grating periodicities are chosen; choosing a periodicity of >600 nm leads for instance to output angles of a magnitude less than about 10° degrees away from normal incidence. Using polarization filters leads to additional improvements in this example.

In summary, the advantages result from the reduction of the size needed per measuring "unit". In addition, there are also the following advantages, whose importance can depend on the actual application:

The chips incorporate a high-density array of individual measuring pads which can be read out in parallel (or sequentially by scanning). This is important for multi-channel parallel detection, for example in biosensing applications or to address each measurement point separately on an array with a high density of pads.

Not only the pads themselves, but also the whole chip has a high functionality.

The invention is applicable for different IO sensing principles (e.g. fluorescence, absorption, scattering, (electro-)chemo-luminescence).

The sensor chips can be fabricated at low-costs due to their smaller size; the same technology can be used for a great variety of applications.

Often, the detector requirements (area) are also relaxed.

Often, the illumination is eased (less area to be illuminated).

What is claimed is:

1. An integrated-optical chemical and/or biochemical sensor comprising:

a resonant waveguide structure;

means for at least temporarily depositing a chemical and/or biochemical substance to be sensed on a surface of said resonant waveguide structure;

means for irradiating said substance with first electromagnetic radiation and for causing said substance to interact with said first electromagnetic radiation in such a way that it emits second electromagnetic radiation which differs in at least one parameter from said first electromagnetic radiation and excites a resonant electromagnetic field in said resonant waveguide structure;

a circular grating structure for coupling out said second electromagnetic radiation from said resonant waveguide structure, said circular grating structure being such that the outcoupling process differs from the irradiating process in the diffraction order, the polarization, the guided-mode order, the grating vector and/or the degree of resonance; and means for detecting second electromagnetic radiation exiting from said resonant waveguide structure.

2. The sensor according to claim 1, wherein said irradiating means comprise a grating structure.

3. The sensor according to claim 2, wherein said irradiating grating structure (G) is identical with said outcoupling circular grating structure.

4. The sensor according to claim 1, wherein said outcoupling circular grating structure is a focusing circular grating structure.

5. The sensor according to claim 1, wherein said irradiating means comprise a grating structure making use of a first diffraction order, and wherein said outcoupling means comprise a grating structure making use of a second diffraction order which is different from said first diffraction order.

6. The sensor according to claim 1, wherein said irradiating means are for irradiating said substance with electromagnetic radiation at a first polarization, and wherein said outcoupling means are for coupling out electromagnetic radiation at a second polarization which is different from said first polarization.

7. The sensor according to claim 4, wherein said irradiating means are for exciting an electromagnetic guided wave, having a first mode order in said resonant waveguide structure, and wherein said circular grating structure is for coupling out an electromagnetic guided wave having a second mode order, which is different from said first mode order, from said resonant waveguide structure.

8. A one-or two-dimensional array of sensors according to claim 1.

9. A method for integrated-optically sensing a chemical and/or biochemical substance using a resonant waveguide structure, comprising the steps of:

at least temporarily depositing said chemical and/or biochemical substance on a surface of said resonant waveguide structure;

irradiating said substance with first electromagnetic radiation;

causing said substance to interact with said first electromagnetic radiation in such a way that it emits second electromagnetic radiation which differs in at least one parameter from said first electromagnetic radiation;

causing said second electromagnetic radiation to excite a resonant electromagnetic field in said resonant waveguide structure;

coupling said second electromagnetic radiation out from said resonant waveguide structure such that the out-coupling process differs from the irradiating process in at least one of a diffraction order, polarization, guided-mode order, grating vector and degree of resonance, said second electromagnetic radiation being coupled out from said resonant waveguide structure by a circular grating structure; and detecting second electromagnetic radiation.

10. The method according to claim 9, wherein the interaction of said substance with said first electromagnetic radiation comprises luminescence, scattering, absorption, chemiluminescence and/or electrochemiluminescence.

11. The method according to claim 9, wherein said first electromagnetic radiation is coupled into said resonant waveguide structure by a grating structure making use of a first diffraction order, and wherein said second electromagnetic radiation is coupled out from said resonant waveguide structure by a circular grating structure making use of a second diffraction order which is different from said first diffraction order.

12. The method according to claim 9, wherein said first electromagnetic radiation has a first polarization, and wherein said second electromagnetic radiation has a second polarization which is different from said first polarization.

13. The method according to claim 9, wherein said first electromagnetic radiation excites an electromagnetic guided wave, having a first mode order, in said resonant waveguide structure, and wherein said second electromagnetic radiation excites an electromagnetic guided wave, having a second mode order which is different from said first mode order, in said resonant waveguide structure.

* * * * *

UNITED STATES PATENT AND TRADEMARK OFFICE
CERTIFICATE OF CORRECTION

PATENT NO. : 6,483,096 B1
DATED : November 19, 2002
INVENTOR(S) : Rino E. Kunz et al.

It is certified that error appears in the above-identified patent and that said Letters Patent is hereby corrected as shown below:

Title page, Item [54] and Column 1, lines 1 and 2,
Delete "INTEGRATED-OPTICAL CHEMICAL AND BIOCHEMICAL SENSOR" and insert -- INTEGRATED-OPTICAL CHEMICAL AND/OR BIOCHEMICAL SENSOR BASED ON AMPLITUDE EFFECTS --.

Column 8,
Line 15, delete "$T_{Em}$, $TM_m$, =" and insert -- $TE_m$, $TM_m$ = --.

Signed and Sealed this

Twenty-second Day of April, 2003

JAMES E. ROGAN
*Director of the United States Patent and Trademark Office*